United States Patent
Gillespie et al.

(10) Patent No.: US 7,674,246 B2
(45) Date of Patent: Mar. 9, 2010

(54) AUTOMATIC INJECTION AND RETRACTION SYRINGE

(75) Inventors: Richard David Gillespie, Athens, TX (US); Doug Owen Crow, Ben Wheeler, TX (US)

(73) Assignee: West Pharmaceutical Services of Delaware, Inc., Lionville, PA (US)

( * ) Notice: Subject to any disclaimer, the term of this patent is extended or adjusted under 35 U.S.C. 154(b) by 975 days.

(21) Appl. No.: 11/296,973

(22) Filed: Dec. 8, 2005

(65) Prior Publication Data

US 2006/0178631 A1    Aug. 10, 2006

Related U.S. Application Data

(60) Provisional application No. 60/634,486, filed on Dec. 9, 2004.

(51) Int. Cl.
*A61M 5/00* (2006.01)
(52) U.S. Cl. ..................................... 604/181
(58) Field of Classification Search ............. 604/68, 604/192–198, 187, 131–139, 181
See application file for complete search history.

(56) References Cited

U.S. PATENT DOCUMENTS

| | | | |
|---|---|---|---|
| 2,561,233 A | 7/1951 | Ryan et al. |
| 3,306,290 A | 2/1967 | Weltman |
| 3,572,336 A | 3/1971 | Hershberg |
| 3,705,582 A | 12/1972 | Stumpf et al. |
| 3,707,968 A | 1/1973 | Koenig |
| 3,708,089 A | 1/1973 | Holder et al. |
| 3,834,387 A | 9/1974 | Brown |
| 3,901,402 A | 8/1975 | Ayres |
| 4,059,109 A | 11/1977 | Tischlinger |
| 4,445,895 A | 5/1984 | Margulies |
| 4,542,749 A | 9/1985 | Caselgrandi et al. |

(Continued)

FOREIGN PATENT DOCUMENTS

JP    10057483 A    3/1998

(Continued)

OTHER PUBLICATIONS

International Preliminary Report on Patentability for related International Patent Application No. PCT/US05/44411, dated Oct. 6, 2008.

(Continued)

*Primary Examiner*—Manuel A Mendez
(74) *Attorney, Agent, or Firm*—Panitch Schwarze Belisario & Nadel LLP

(57) ABSTRACT

An automatic injection and retraction syringe having a medicine cartridge, an injection assembly, and a retraction assembly is provided. The retraction assembly is selectively securable to the injection assembly to house the medicine cartridge. The retraction assembly includes an end cap, a hypodermic needle, a retraction spring, and an upper seal. The retraction spring is maintained in a partially compressed condition between the needle hub and the end cap. The upper seal is urged against a sealing surface by the retraction spring in the partially compressed condition to form a hermetic seal. In some embodiments, the injection assembly includes an injection spring, a plunger engaged to the injection spring, and a safety element to prevent the plunger from escaping the injection assembly if the injection spring is released from the normally stressed condition before the assemblies are secured to one another.

6 Claims, 16 Drawing Sheets

U.S. PATENT DOCUMENTS

| | | | |
|---|---|---|---|
| 4,581,016 A | 4/1986 | Gettig | |
| D286,164 S | 10/1986 | Tinz | |
| D287,603 S | 1/1987 | Bruhn | |
| 4,643,721 A | 2/1987 | Brunet | |
| 4,689,042 A | 8/1987 | Sarnoff et al. | |
| 4,755,169 A | 7/1988 | Sarnoff et al. | |
| 4,767,413 A * | 8/1988 | Haber et al. | 604/198 |
| 4,795,444 A | 1/1989 | Hasegawa et al. | |
| 4,820,286 A | 4/1989 | Van Der Wal | |
| 4,822,340 A | 4/1989 | Kamstra | |
| 4,861,335 A | 8/1989 | Reynolds | |
| 4,886,495 A | 12/1989 | Reynolds | |
| 4,898,580 A | 2/1990 | Crowley | |
| 4,969,877 A | 11/1990 | Kornberg | |
| 4,998,922 A | 3/1991 | Karucina et al. | |
| 5,049,133 A | 9/1991 | Villen Pascual | |
| 5,085,641 A | 2/1992 | Sarnoff et al. | |
| 5,085,642 A | 2/1992 | Sarnoff et al. | |
| 5,092,843 A | 3/1992 | Monroe et al. | |
| 5,102,393 A | 4/1992 | Sarnoff et al. | |
| 5,120,310 A | 6/1992 | Shaw | |
| 5,137,511 A | 8/1992 | Reynolds | |
| 5,169,385 A | 12/1992 | Turnbull | |
| 5,176,657 A | 1/1993 | Shields | |
| 5,188,613 A | 2/1993 | Shaw | |
| D339,606 S | 9/1993 | Podobrin | |
| 5,267,961 A | 12/1993 | Shaw | |
| 5,295,965 A | 3/1994 | Wilmot | |
| 5,300,030 A | 4/1994 | Crossman et al. | |
| 5,324,273 A | 6/1994 | Discko, Jr. | |
| 5,358,489 A | 10/1994 | Wyrick | |
| 5,364,363 A | 11/1994 | Pearson et al. | |
| 5,383,865 A | 1/1995 | Michel | |
| 5,385,551 A | 1/1995 | Shaw | |
| 5,389,076 A | 2/1995 | Shaw | |
| 5,391,151 A | 2/1995 | Wilmot | |
| 5,411,487 A | 5/1995 | Castagna | |
| 5,411,489 A | 5/1995 | Pagay et al. | |
| 5,413,564 A | 5/1995 | Silver et al. | |
| 5,423,758 A | 6/1995 | Shaw | |
| 5,425,715 A | 6/1995 | Dalling et al. | |
| 5,466,223 A | 11/1995 | Bressler et al. | |
| 5,531,255 A | 7/1996 | Vacca | |
| 5,540,664 A | 7/1996 | Wyrick | |
| 5,545,145 A | 8/1996 | Clinton et al. | |
| 5,578,011 A | 11/1996 | Shaw | |
| 5,599,309 A | 2/1997 | Marshall | |
| 5,620,421 A | 4/1997 | Schmitz | |
| 5,632,733 A | 5/1997 | Shaw | |
| 5,637,092 A | 6/1997 | Shaw | |
| 5,643,214 A | 7/1997 | Marshall | |
| 5,665,071 A | 9/1997 | Wyrick | |
| 5,674,204 A | 10/1997 | Chanoch | |
| 5,685,846 A | 11/1997 | Michaels, Jr. | |
| 5,688,251 A | 11/1997 | Chanoch | |
| 5,695,472 A | 12/1997 | Wyrick | |
| 5,779,677 A | 7/1998 | Frezza | |
| 5,779,679 A | 7/1998 | Shaw | |
| 5,810,775 A | 9/1998 | Shaw | |
| 5,817,058 A | 10/1998 | Shaw | |
| RE35,986 E | 12/1998 | Ritson et al. | |
| 5,860,961 A | 1/1999 | Gettig | |
| 5,873,462 A | 2/1999 | Nguyen et al. | |
| 5,921,966 A | 7/1999 | Bendek et al. | |
| 5,931,817 A | 8/1999 | Nguyen et al. | |
| 5,941,857 A | 8/1999 | Nguyen et al. | |
| 5,944,700 A | 8/1999 | Nguyen et al. | |
| D414,201 S | 9/1999 | Larson et al. | |
| 5,957,896 A | 9/1999 | Bendek et al. | |
| 5,957,897 A | 9/1999 | Jeffrey | |
| D414,807 S | 10/1999 | Baudino et al. | |
| 5,961,495 A | 10/1999 | Walters et al. | |
| 5,989,220 A | 11/1999 | Shaw et al. | |
| 5,997,512 A | 12/1999 | Shaw | |
| 6,001,082 A | 12/1999 | Dair et al. | |
| 6,015,438 A | 1/2000 | Shaw | |
| D423,577 S | 4/2000 | Baudino et al. | |
| D425,120 S | 5/2000 | Ramil | |
| 6,086,563 A | 7/2000 | Moulton et al. | |
| 6,095,814 A | 8/2000 | Petrich et al. | |
| 6,099,503 A | 8/2000 | Stradella | |
| 6,149,623 A | 11/2000 | Reynolds | |
| 6,183,445 B1 | 2/2001 | Lund et al. | |
| 6,200,627 B1 | 3/2001 | Lubrecht | |
| 6,210,315 B1 | 4/2001 | Andrews et al. | |
| 6,210,371 B1 | 4/2001 | Shaw et al. | |
| 6,213,597 B1 | 4/2001 | Liu | |
| 6,221,046 B1 | 4/2001 | Burroughs et al. | |
| 6,221,053 B1 | 4/2001 | Walters et al. | |
| 6,221,055 B1 | 4/2001 | Shaw et al. | |
| D441,398 S | 5/2001 | Owen et al. | |
| 6,248,095 B1 | 6/2001 | Giambattista et al. | |
| D446,242 S | 8/2001 | Stukenkemper | |
| 6,277,099 B1 | 8/2001 | Strowe et al. | |
| D452,271 S | 12/2001 | Owen et al. | |
| 6,328,715 B1 | 12/2001 | Dragan et al. | |
| 6,346,094 B2 | 2/2002 | West et al. | |
| 6,349,850 B1 | 2/2002 | Cheikh | |
| 6,387,078 B1 | 5/2002 | Gillespie | |
| 6,494,863 B1 | 12/2002 | Shaw et al. | |
| 6,572,584 B1 | 6/2003 | Shaw et al. | |
| 6,638,244 B1 | 10/2003 | Reynolds | |
| 6,689,118 B2 | 2/2004 | Alchas et al. | |
| 6,793,646 B1 | 9/2004 | Giambattista et al. | |
| 6,796,967 B2 | 9/2004 | Jensen | |
| 6,802,828 B2 | 10/2004 | Reynolds | |
| 2001/0002434 A1 | 5/2001 | Lubrecht | |
| 2001/0029354 A1 | 10/2001 | Rolle et al. | |
| 2001/0039400 A1 | 11/2001 | Lubrecht | |
| 2002/0010430 A1 | 1/2002 | Dragan et al. | |
| 2002/0164265 A1 | 11/2002 | Hetzler | |
| 2002/0177819 A1 | 11/2002 | Barker et al. | |
| 2003/0083621 A1 | 5/2003 | Shaw et al. | |
| 2003/0100866 A1 | 5/2003 | Reynolds | |
| 2003/0130626 A1 | 7/2003 | VanTassel et al. | |
| 2003/0187388 A1 | 10/2003 | Sharon et al. | |
| 2004/0024367 A1 | 2/2004 | Gilbert | |
| 2004/0111064 A1 | 6/2004 | Asbaghi | |
| 2005/0049551 A1 | 3/2005 | Kirchhofer | |
| 2005/0113763 A1 | 5/2005 | Reynolds | |
| 2006/0178629 A1 | 8/2006 | Gillespie et al. | |
| 2006/0178631 A1 | 8/2006 | Gillespie et al. | |

OTHER PUBLICATIONS

International Search Report and Written Opinion for related International Patent Application PCT/US05/44411, dated Jun. 21, 2007.
International Search Report for related International Patent Application No. PCT/US05/44492 and written opinion; dated May 25, 2006.
International Search Report and Written Opinion for related International Patent Application No. PCT/US08/52427; dated Aug. 4, 2008.
International Search Report and Written Opinion for related International Patent Application No. PCT/US05/44410; dated Jun. 27, 2006.
International Search Report for related International Patent Application No. PCT/US06/27733, dated Apr. 23, 2007.
Office Action for related Chinese Patent Application No. 200580047001.0 issued Jul. 17, 2009.
First Office Action for related Chinese patent Application No. 200580047294.2; mailed Aug. 21, 2009; 7 pages (English translation only).

* cited by examiner

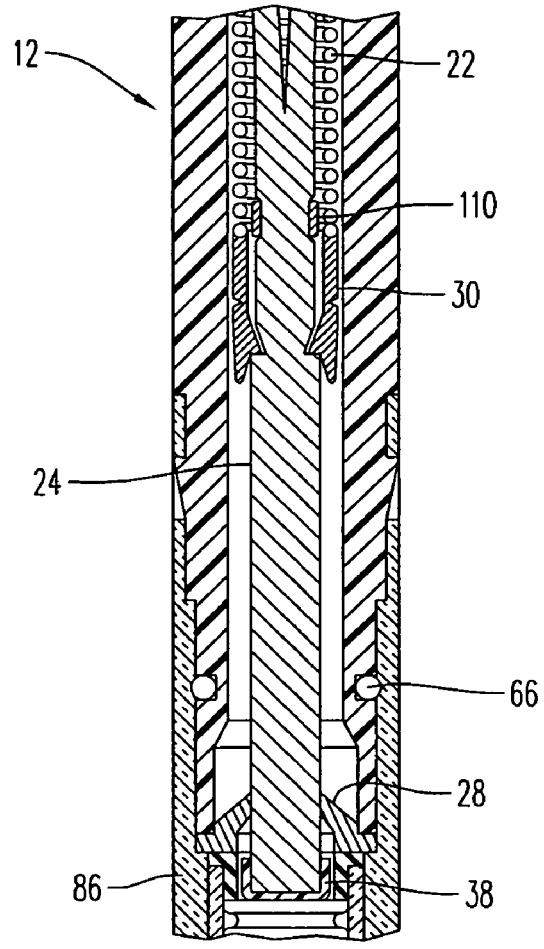 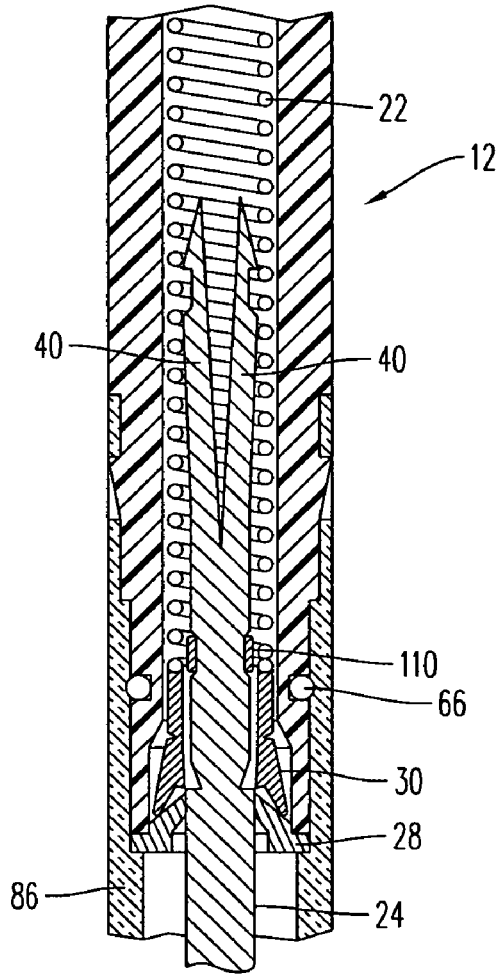
FIG. 11     FIG. 12

AUTOMATIC INJECTION AND RETRACTION SYRINGE

CROSS REFERENCE TO RELATED APPLICATIONS

This application claims priority of U.S. Provisional Application Ser. No. 60/634,486 filed on Dec. 9, 2004 and is related to commonly owned and assigned U.S. application Ser. No. 10/601,212, filed Jun. 20, 2003, the contents of both of which are incorporated by reference herein.

BACKGROUND OF THE INVENTION

1. Field of the Invention

The present disclosure is related to an automatic injection and retraction syringe. More particularly, the present disclosure is related to an automatic injection and retraction syringe having a retraction assembly and an injection assembly that are selectively connectable to one another.

2. Description of Related Art

Diseases such as AIDS, Hepatitis, and others, are increasing within the general population. The onset of these diseases has increased the desire to prevent inadvertent needle sticks during the use of syringe assemblies. Many prior art devices include self-retracting needles to mitigate inadvertent needle sticks.

Many life-threatening situations such as allergy-induced anaphylactic shock, and exposure to chemical, radiological, and biological weapons, can require the use of automatic injection devices. Typical automatic injection devices are syringe assemblies that allow the medically untrained user to automatically inject a medicine by manually trigging the automatic injection. Some prior automatic injection devices also incorporate self-retracting needles.

There is a continuing need for improved automatic injection and retraction syringes.

BRIEF SUMMARY OF THE INVENTION

It is an object of the present disclosure to provide an automatic injection and retraction syringe having a selectively connectable injection assembly and retraction assembly.

It is another object to provide an automatic injection and retraction syringe having an injection and retraction assembly hermetically sealed to one another.

It is yet another object to provide an automatic injection and retraction syringe having a retraction assembly with a hermetically sealed hypodermic needle.

It is still another object to provide retraction assembly having an automatic injection and retraction syringe having a retraction spring that maintains a hermetic seal in a desired position prior to use and retracts a hypodermic needle back into the retraction assembly after use.

It is another object to provide an automatic injection and retraction syringe having an injection assembly with a safety element to prevent a plunger from being ejected from the injection assembly prior to final assembly.

It is yet another object to provide an automatic injection and retraction syringe having a composite plunger with a stamped metallic locking end and a molded plastic driving end.

It is still a further object to provide an automatic injection and retraction syringe having plunger with an integrally molded safety element.

An automatic injection and retraction syringe is provided. The syringe includes a medicine cartridge, an injection assembly, and a retraction assembly. The retraction assembly is selectively securable to the injection assembly to house the medicine cartridge therein. The retraction assembly includes an end cap with a penetrable elastomeric seal, a hypodermic needle, a retraction spring, and an upper seal. The retraction spring is maintained in a partially compressed condition between the needle hub and the end cap. The upper seal is urged against a facially sealing surface of the retraction assembly by the retraction spring in the partially compressed condition to form a first hermetic seal.

An automatic injection and retraction syringe is also provided with an injection assembly that includes an injection spring, a plunger drivingly engaged to the injection spring by way of a coupling element, and a safety element defined on the plunger. The safety element prevents the plunger from escaping the injection assembly if the injection spring is released from the normally stressed condition before the retraction assembly is secured to the injection assembly.

An injection kit is provided that includes an injection assembly and a retraction assembly that are selectively securable to one another. The kit can include a medicine cartridge for receipt in the injection and retraction assemblies when the assemblies are secured to one another. The kit can include at least one injection site cleaning swab and/or an adhesive bandage.

The above-described and other features and advantages of the present disclosure will be appreciated and understood by those skilled in the art from the following detailed description, drawings, and appended claims.

BRIEF DESCRIPTION OF THE SEVERAL VIEWS OF THE DRAWINGS

FIG. 11 is a close up sectional view of an exemplary embodiment of a injection assembly according to the present disclosure before activation;

FIG. 12 is a sectional view of the injection assembly of FIG. 11 after activation, and immediately prior to retraction;

DETAILED DESCRIPTION OF THE INVENTION

Figure 1:
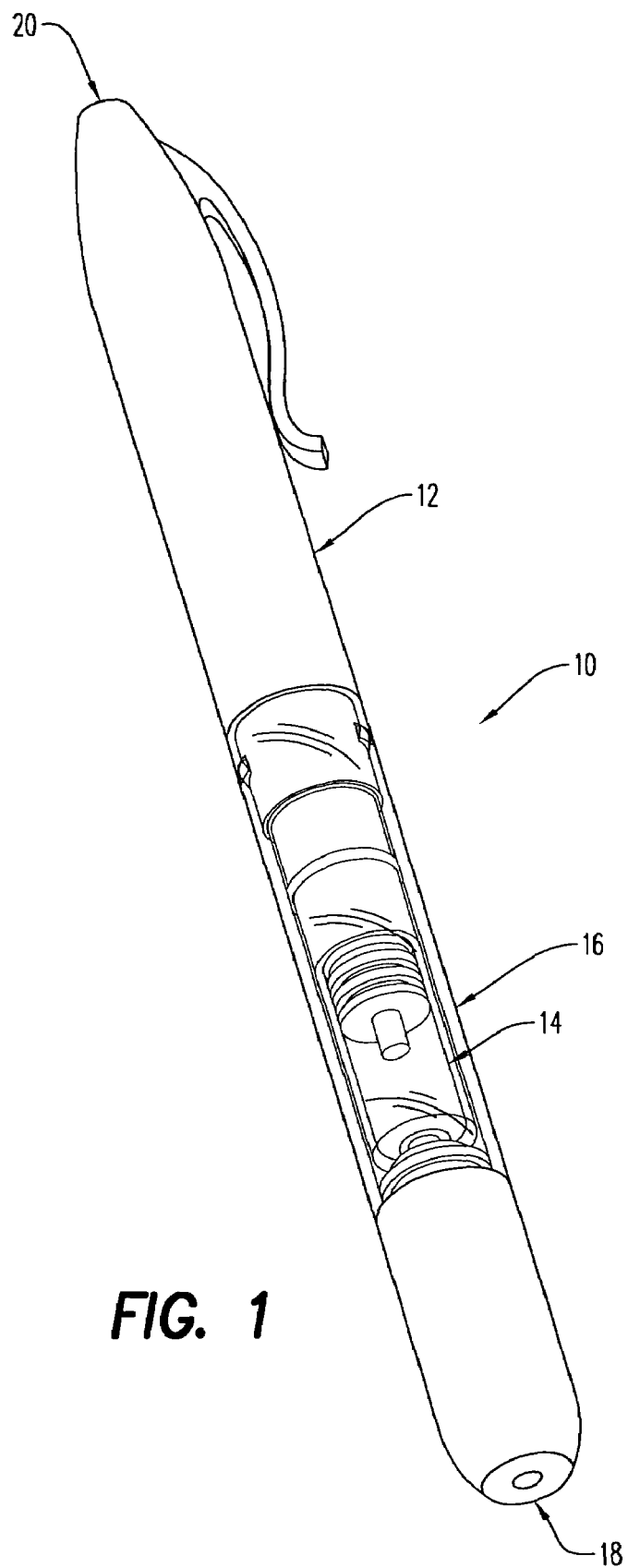
FIG. 1 is a perspective view of an exemplary embodiment of a syringe according to the present disclosure.
Figure 2:
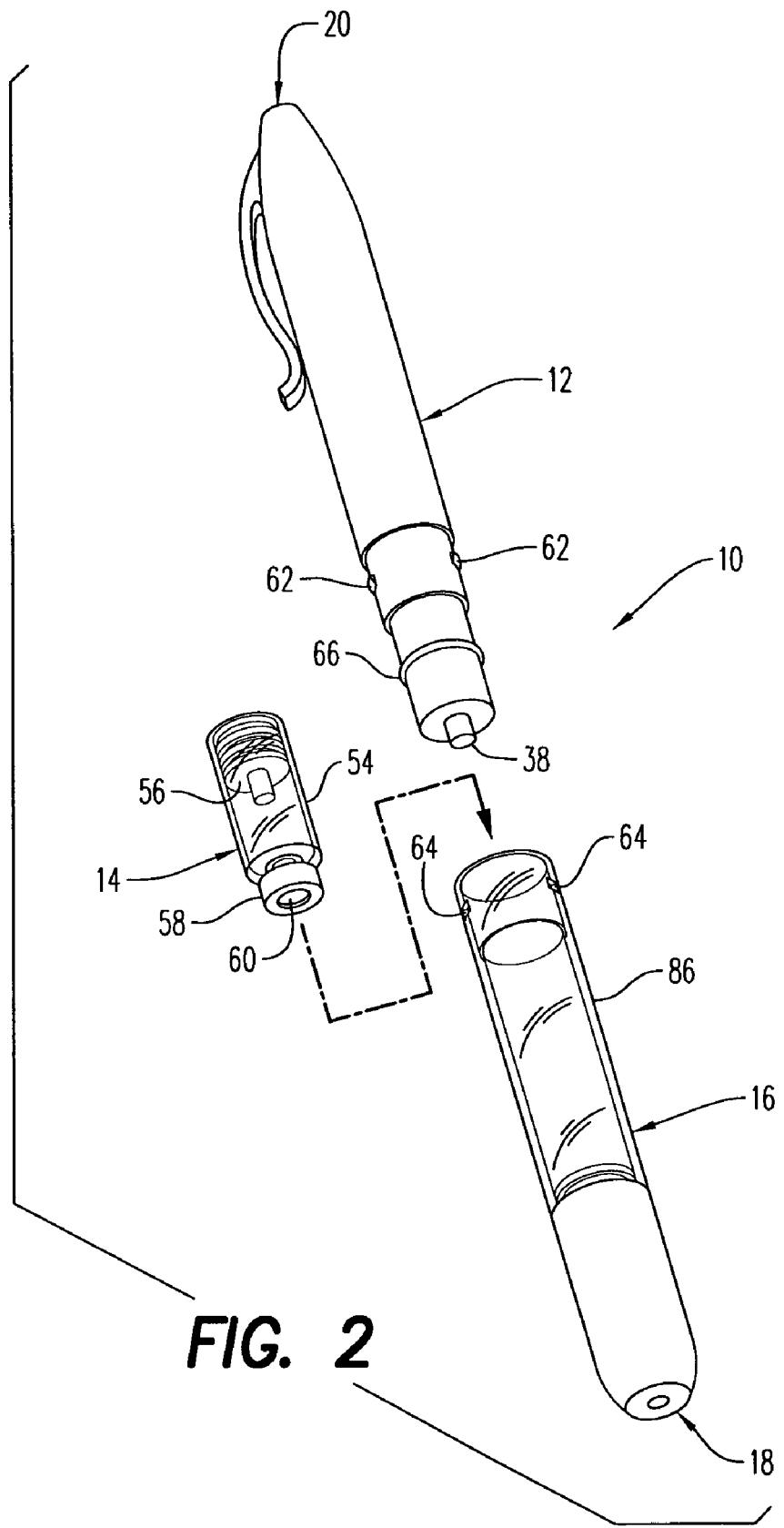
FIG. 2 is an exploded view of the syringe of FIG. 1
Figure 3:
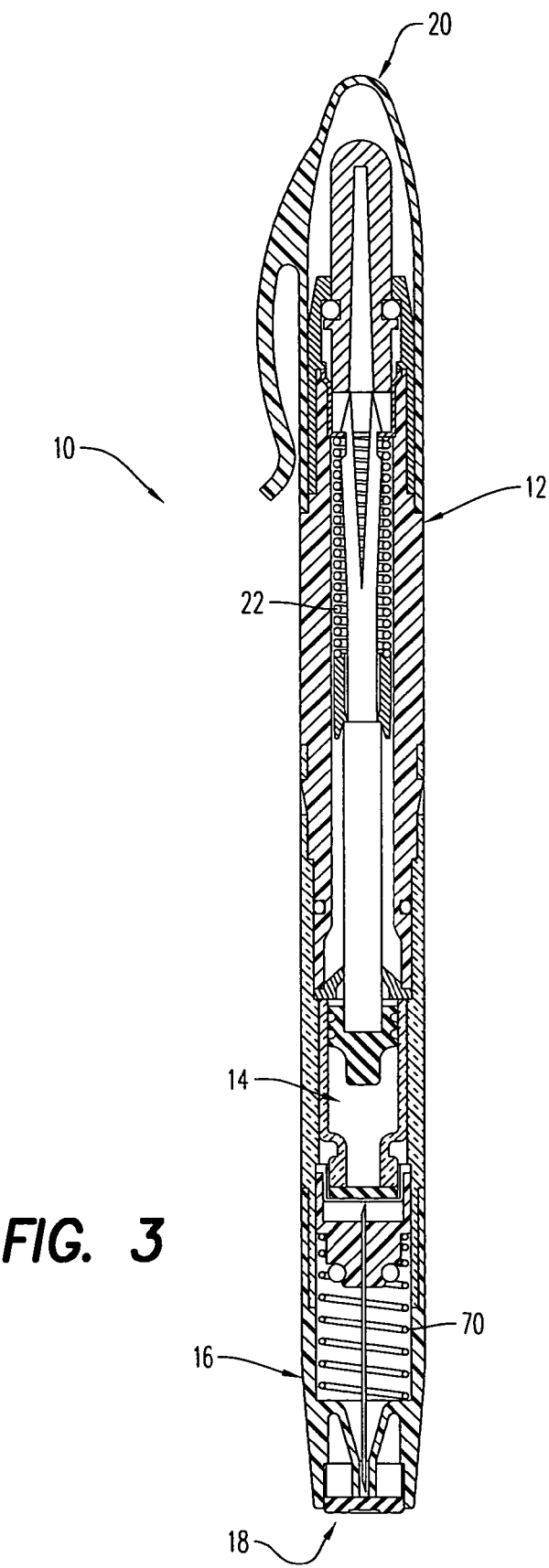
FIG. 3 is a sectional view of the syringe of FIG. 1.

Referring to the figures and in particular to FIGS. 1 through 3, an exemplary embodiment of a syringe 10 according to the present disclosure is shown. Syringe 10 includes an injection assembly 12, a medicine cartridge 14, and a retraction assembly 16.

Referring to FIG. 2, advantageously, syringe 10 is a multi-component device that can be assembled by the user or healthcare provider (e.g., pharmacist, doctor, nurse). Since exemplary embodiments of syringe 10 do not require assembly at the time of manufacture, the present disclosure effectively separates expiry of medicine cartridge 14 from the expiry of syringe 10. For example, typical flu vaccines have an expiration date of one year. Thus, the user can maintain a supply of injection assembly 12 and retraction assembly 16 of the present disclosure, while only replacing any expired medicine cartridges 14.

Syringe 10 is, preferably, an automatic injection apparatus that extends a hypodermic needle from within the assembly, injects a single, pre-measured dose of medicine from cartridge 14 into a user, and automatically retracts the hypodermic needle into the assembly after the injection is completed. Syringe 10 defines an injection end 18 for placement against the user and an activation end 20 for activating injection assembly 12.

The operation of injection assembly 12 is described with reference to FIG. 4. Injection assembly 12 includes an injection spring 22, a plunger 24, an activation button 26, a de-coupler 28, and a coupling 30. Injection spring 22 is disposed about plunger 24 between capture 42 and coupling 30. Injection spring 22 is drivingly engaged to plunger 24 by coupling 30.

Activation button 26 is defined at activation end 20. Activation button 26 has an upper end 32 and a lower end 34. Upper end 32 protrudes outwardly from injection assembly 12. Lower end 34 extends inwardly and is configured to selectively disengage the plunger 24 from engagement with locking surface 44 in order to release the energy in injection spring 22 and propel plunger 24. In the illustrated embodiment, plunger 24 includes a locking end 36 and a driving end 38. Locking end 36 includes two or more tines 40 that are resiliently biased outward so that the tines are remote from one another. Driving end 38 is configured to act on medicine cartridge 14 as will be described in detail below.

Injection assembly 12 includes a capture 42 that engages a locking surface 44 of tines 40 when biased from one another. Activation button 26 includes a releasing surface 46 defined at lower end 34. Force applied to upper end 32 of activation button 26 causes releasing surface 46 to compress fork tines 40 toward one another such that locking surfaces 44 are disengaged from capture 42, which remains in a fixed position within the injection assembly 12.

Plunger 24 maintains injection spring 22 in a normally compressed or stressed condition between coupling 30 and capture 42. Upon release of tines 40 from capture 42, the stored energy in spring 22 propels plunger 24 in an injection direction 48. As the plunger 24 moves in direction 48 under the influence of the injection spring 22, the retraction assembly 16 becomes energized.

Injection spring 22 propels plunger 24 in injection direction 48 until coupling 30 slideably abuts de-coupler 28. The force of injection spring 22 upon coupling 30 causes the coupling to engage de-coupler 28 so that the coupling flares open and disengages from its radial interference engagement with plunger 24. The disengagement of coupling 30 from plunger 24 terminates the influence of injection spring 22 on plunger 24 and allows the plunger to be moved in a retraction direction 50 by the action of the energized retraction assembly 16.

Syringe 10 can be configured to inject medicine from cartridge 14 intramuscularly, subcutaneously and/or intradermally. For example, de-coupler 28 can be secured in injection assembly 12 for movement along injection direction 48 and/or retraction direction 50. Movement of de-coupler 28 can change the stroke of injection assembly 12 by changing the point at which the de-coupler uncouples injection spring 22 from plunger 24.

Figure 4:
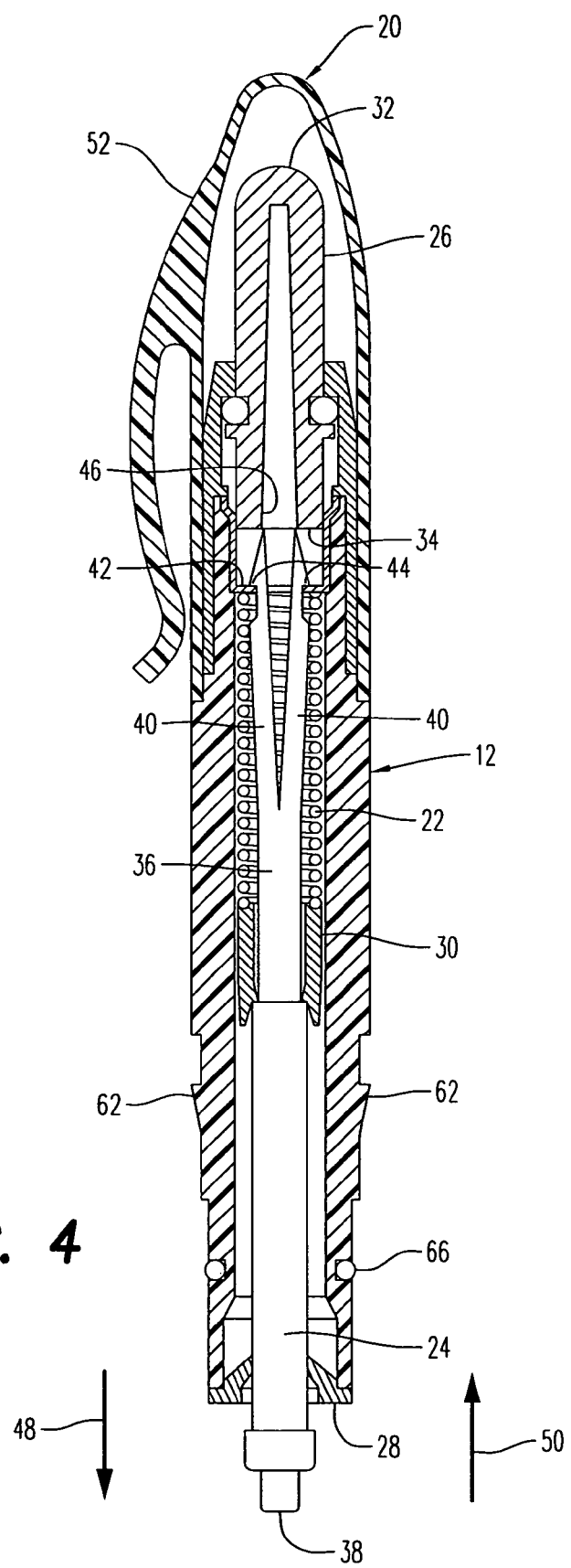
FIG. 4 is a sectional view of an exemplary embodiment of an injection assembly according to the present disclosure.
Figure 5:
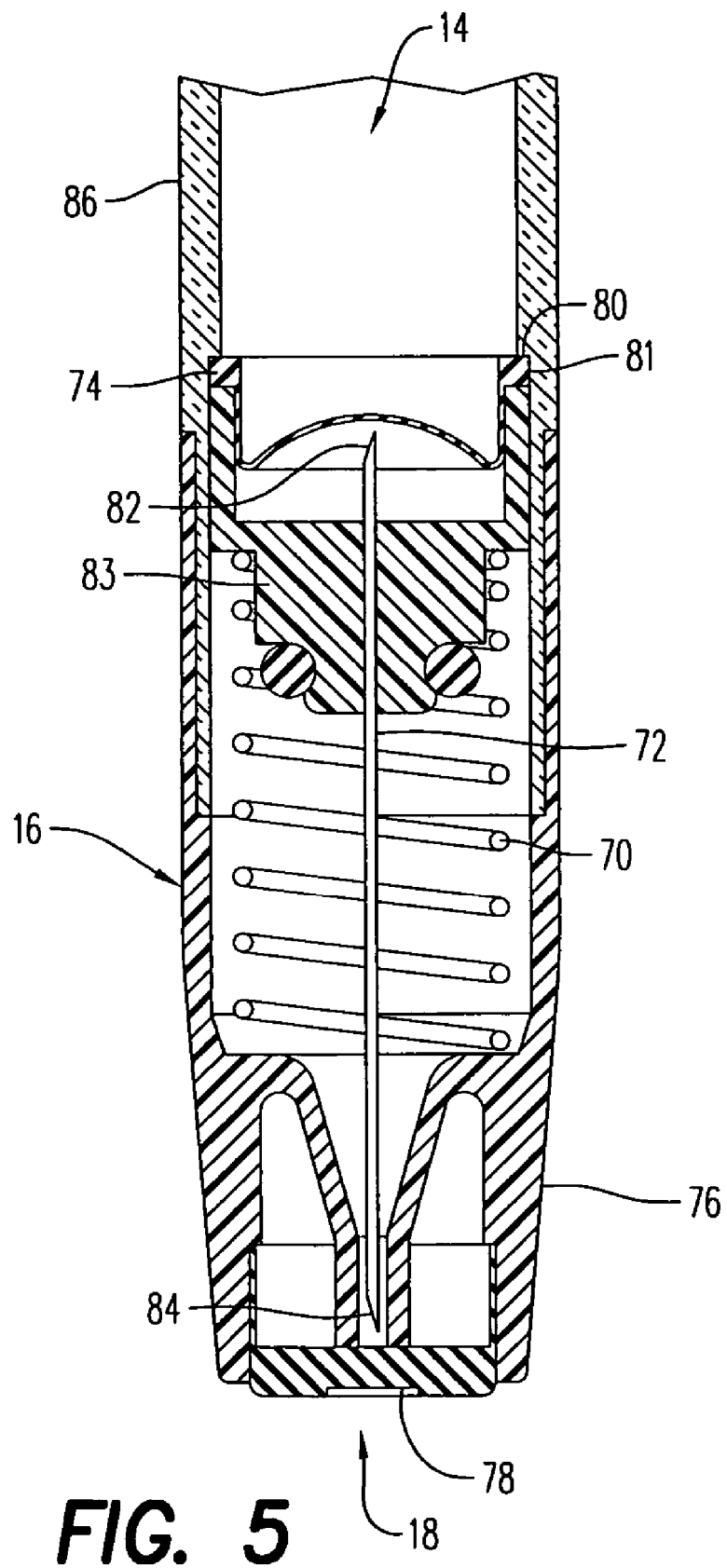
FIG. 5 is a sectional view of an exemplary embodiment of a retraction assembly for use with the syringe of FIG. 1 prior to installation of a medicine cartridge.

Referring to the illustrated embodiment in FIG. 4, injection assembly 12 includes a safety cap 52 that is disposed over activation button 26. Safety cap 52 can mitigate inadvertent depression of activation button 26 and, thus, can prevent premature activation of injection assembly 12.

As discussed above, syringe 10 does not require assembly at the time of manufacture. The assembly of syringe 10 is discussed with reference to FIG. 2. Cartridge 14 includes a medicine vial 54, a movable piston 56, and an end cap 58. End cap 58 includes a pierceable septum 60.

Cartridge 14 is inserted into retraction assembly 16 so that end cap 58 is towards injection end 18 and piston 56 is towards activation end 20. Once cartridge 14 is installed in retraction assembly 16, the retraction assembly and injection assembly 12 can be operatively secured to one another. In the assembled position, activation of injection assembly 12 causes driving end 38 of plunger 24 to move in injection direction 48 into contact with piston 56. Because the fluid medicament inside cartridge 14 is incompressible, the force applied to piston 56 by plunger 24 causes translation of cartridge 14 in injection direction 48. Translation of cartridge in injection direction 48 energizes retraction spring 70 and causes hypodermic needle 72 to penetrate lower seal 78 and the tissue at the injection site. Then, pierceable septum 60 is punctured and piston 56 expels the medicine from cartridge 14.

In a preferred embodiment, injection assembly 12 and retraction assembly 16 are permanently secured to one another in a snap fit manner so that the assemblies can not be removed from one another after injection. For example, and referring to FIGS. 4 and 10; injection assembly 12 can include one or more outwardly depending tabs 62 that are received in a corresponding number of openings 64 defined in retraction assembly 16. As injection assembly 12 is inserted into retraction assembly 16, tabs 62 act on the retraction assembly to resiliently deform the inner dimension of the tube. Once tabs 62 are received by openings 64, the inner dimension of retraction assembly 16 returns to its original dimension to secure the tabs in the openings.

In the assembled state, injection assembly 12 and retraction assembly 16 preferably maintain cartridge 14 hermetically sealed therebetween. For example, injection assembly 12 can include a sealing member 66 such as, but not limited to an o-ring. Once injection assembly 12 and retraction assembly 16 are secured together, sealing member 66 elastically cooperates with the interior of the retraction assembly 16 and exterior surface of injection assembly 12 to form a hermetic radial seal. In the illustrated embodiment, sealing member 66 is positioned below openings 64 defined in retraction assembly 16 to provide the hermetic seal below the snap fit connection between tabs 62 and openings 64.

Referring now to FIGS. 5 through 8, retraction assembly 16 is designed to cooperate with cartridge 14 and includes a tubular section 86, a retraction spring 70, a hypodermic needle 72, an upper seal 74, a needle hub 83, an end cap 76, and a lower seal 78.

Upper seal 74 is configured to receive cap 58 of cartridge 14. Upper seal 74 is configured to form a hermetic seal against a facial sealing surface 80 and/or a radial sealing surface 81 defined in an inner diameter of retraction assembly 16.

Before activation of syringe 10, retraction spring 70 is partially biased between needle hub 83 and end cap 76. For reasons described herein below, retraction spring 70 has a lower spring rate than injection spring 22. In the partially biased condition, retraction spring 70 urges needle hub 83 in a direction opposite injection direction 48 to maintain upper seal 74 in contact with and, thus, sealed against facial sealing surface 80. Prior to activation, hypodermic needle 72 remains fully within the sealed volume between upper and lower seals 74, 78.

In this condition, retraction spring 70 maintains upper seal 74 hermetically sealed against sealing surface 80 in retraction assembly 16. Thus, retraction assembly 16 can be terminally sterilized during manufacture so that a sterile volume between upper and lower seals 74, 78, including hypodermic needle 72, is maintained until use.

Needle 72 is a double-ended hypodermic needle that includes a first or medicine entrance tip 82 and a second or tissue penetrating and medicine exit tip 84. Entrance tip 82 is positioned proximate to upper seal 74, while exit tip 84 is positioned proximate to lower seal 78.

During use of syringe 10, the movement of plunger 24 urges medicine cartridge 14 in injection direction 48 towards upper seal 74 so that entrance tip 82 pierces the upper seal and septum 60 to place the needle in fluid communication with the cartridge. Because the medicament within medicine cartridge 14 is an incompressible fluid, further movement of plunger 24 also urges needle 72 in injection direction 48 by overcoming the force of retraction spring 70. Thus, exit tip 84 pierces lower seal 78 and is inserted into the tissue at the injection site. Finally, the movement of plunger 24 urges plunger 24 in injection direction 48 so that medicine in cartridge 14 is expelled into the user through exit tip 84.

Figure 6:
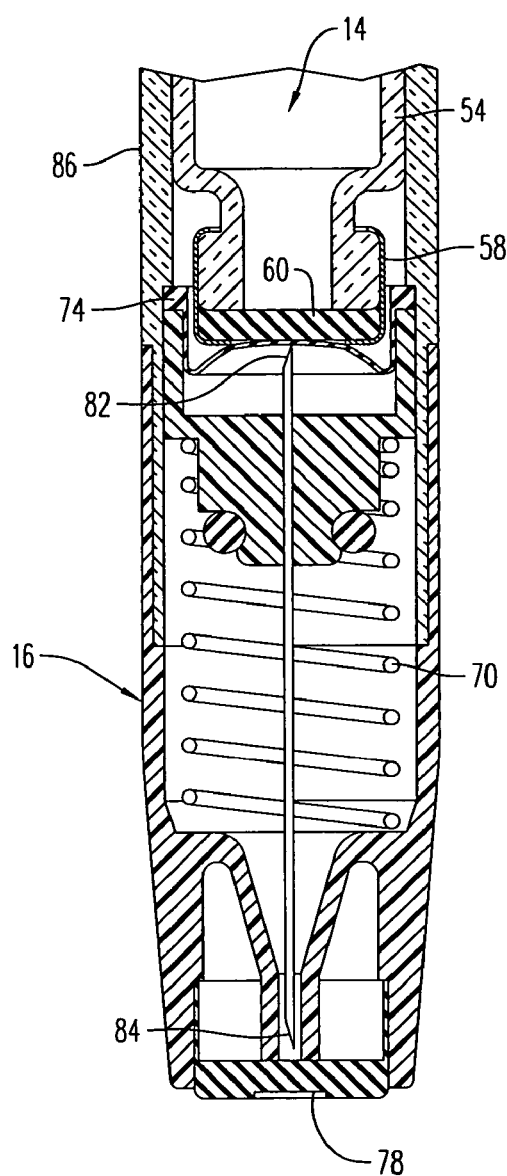
FIG. 6 is a sectional view the retraction assembly of FIG. 5 after installation of a medicine cartridge.

For example, syringe 10 is shown in FIG. 6 in a fully assembled state where cartridge 14 is positioned in retraction assembly 16 and injection assembly 12 is secured to the retraction assembly. Here, end cap 58 is sealing engaged by upper seal 74 so that septum 60 of the end cap is aligned with first tip 82.

Figure 7:
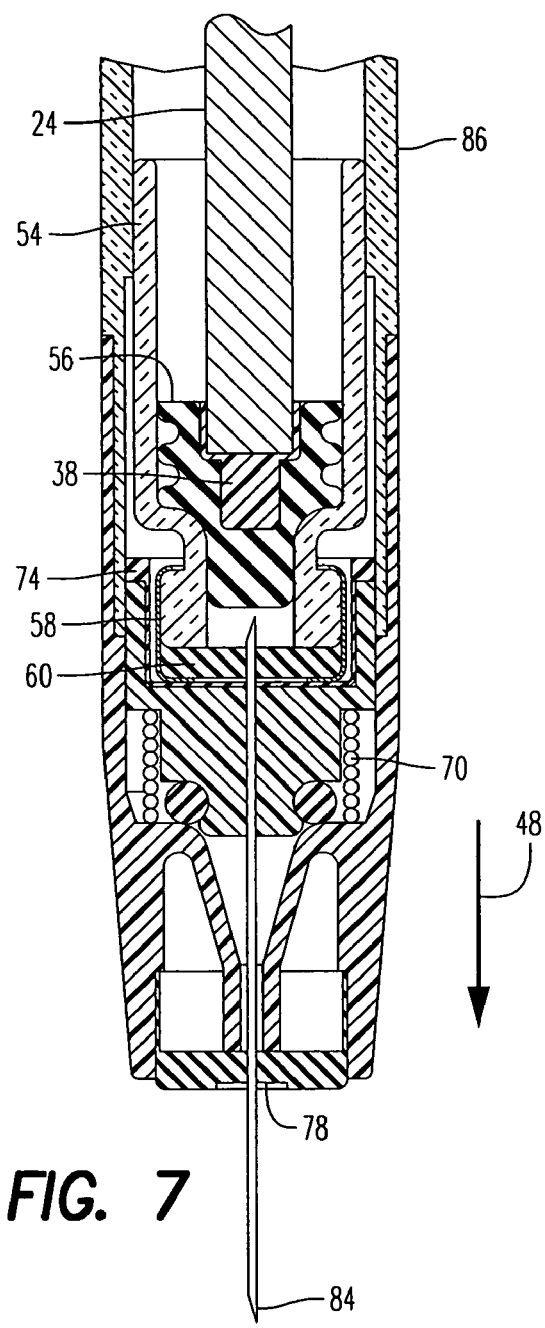
FIG. 7 is a sectional view of the retraction assembly of FIG. 5 after injection and prior to retraction.

In FIG. 7, syringe 10 is shown after activation of injection assembly 12. Here, injection spring 22 has driven plunger 24 into medicine cartridge 14 so that driving end 38 of the plunger engages piston 56. Injection spring 22 has overcome the force of retraction spring 70 to compress the retraction spring and has moved cartridge 14 in injection direction 48 so that end cap 58 deforms upper seal 74 into first tip 82. In this manner, first tip 82 pierces both upper seal 74 and septum 60 to place needle 72 in fluid communication with cartridge 14.

Injection spring 22 has moved needle 72 in injection direction 48 so that second tip 84 pierces lower seal 78 and enters the skin of the user. In addition, injection spring 22 has moved driving end 38 of plunger 24 in injection direction 48 to expel medicine from the cartridge through second tip 84.

Figure 8:
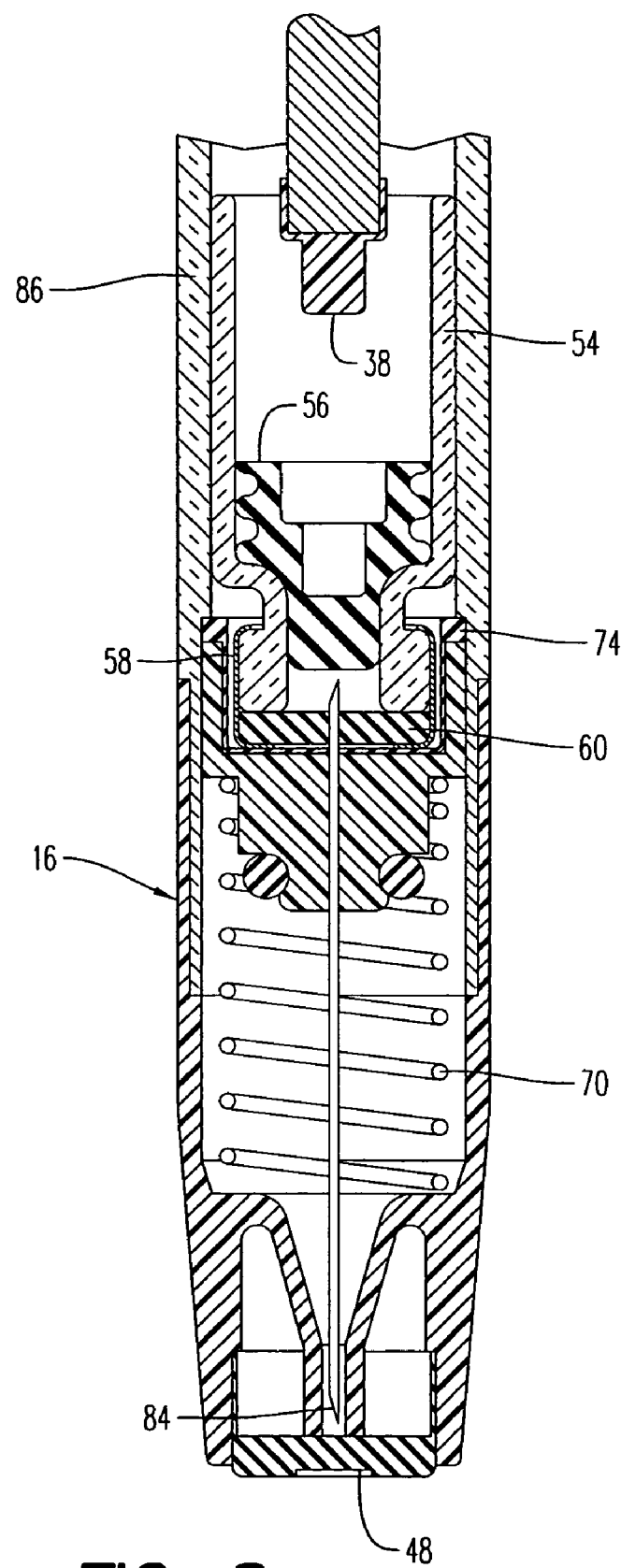
FIG. 8 is a sectional view of the retraction assembly of FIG. 5 after retraction.

At the point where piston 56 has been moved to complete the injection of medicine from cartridge 14, plunger 24 has moved in injection direction 48 a sufficient amount to cause de-coupler 28 to disengage coupling 30, and thus injection spring 22, from plunger 24. Once injection spring 22 is disengaged, retraction spring 70 urges needle 72, cartridge 14, and the plunger 24 in retraction direction 50 back into retraction assembly 16 as seen in FIG. 8. In the embodiment where injection assembly 12 is permanently secured to retraction assembly 16, retraction of needle 72 into the retraction assembly renders syringe 10 safe from exposing anyone that may handle the syringe after use from inadvertent injury by the used needle and, thus, safe for disposal.

In one embodiment of retraction assembly 16, tubular section 86 can be transparent. Once syringe 10 is assembled, transparent tubular section 86 allows users and medical providers to view cartridge 14, to verify correct dose volume in the cartridge, to verify drug solution has not degraded, and after use to confirm the full dose was administered.

Advantageously, retraction assembly 16 maintains a double-sided needle hermetically sealed therein. Thus, retraction assembly 16 can be terminally sterilized and maintained in the sterile condition separate from medicine cartridge 14. Once syringe 10 is assembled, medicine cartridge 14 is hermetically sealed between injection assembly 12 and retraction assembly 16.

In one embodiment of the present disclosure, syringe 10 can be provided in an unassembled state in a terminally sterilized kit (not shown) for assembly and use. Here, the kit can include injection assembly 12 and retraction assembly 16. In some embodiments, the kit can include medicine cartridge 14, but in others the medicine cartridge can be sold separately. In addition, the kit can also include one or more injection site cleaning swabs, such as pre-packaged alcohol swabs. For example, injection assembly 12, retraction assembly 16, and the cleaning swabs can be contained in a sealed package, such as a plastic or TYVEC package. In some embodiments, the package can be terminally sterilized.

Figure 9:
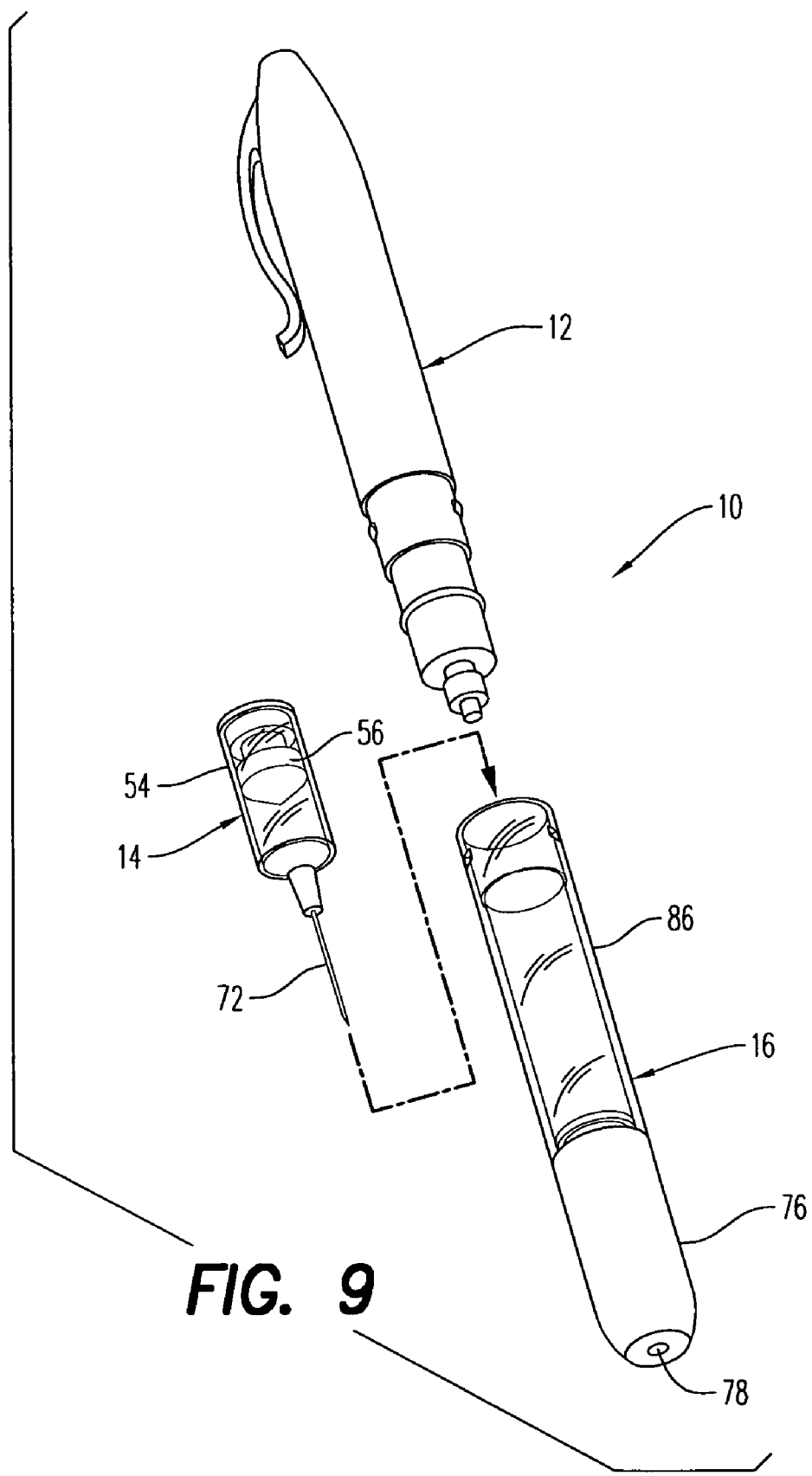
FIG. 9 is an exploded view of an alternate exemplary embodiment of a syringe according to the present disclosure.
Figure 10:
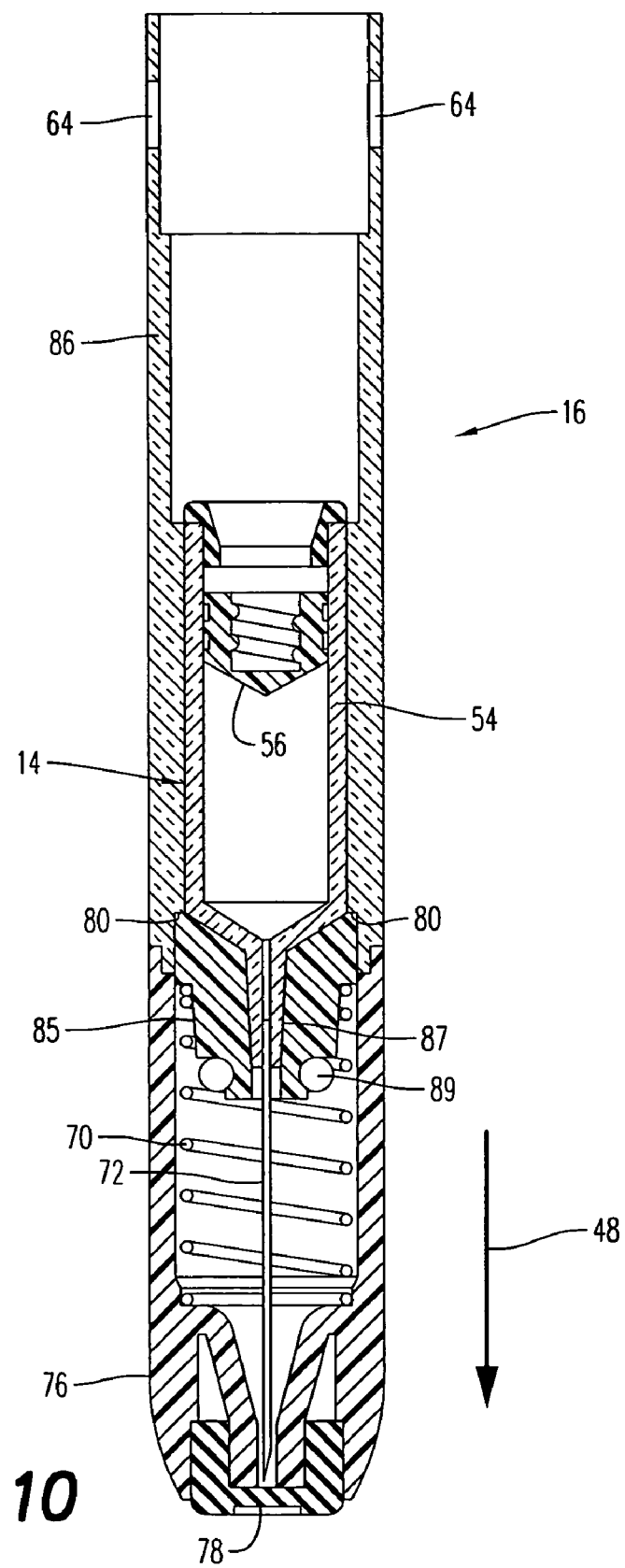
FIG. 10 is a sectional view of a retraction assembly for use with the syringe of FIG. 9 after installation of a medicine cartridge.

Referring now to FIGS. 9 and 10, an alternate exemplary embodiment of a syringe 10 according to the present disclosure is shown. Syringe 10 includes an injection assembly 12, a medicine cartridge 14, and a retraction assembly 16. Here, injection assembly 12 is as described above with respect to FIGS. 1 through 8.

In this embodiment, medicine cartridge 14 includes medicine vial 54 and movable piston 56, as well as a single tipped needle 72 integrally formed therewith. Here, medicine cartridge 14 can be filled with medicine at the time of use or prior to assembly of syringe 10.

Cartridge 14 is inserted into retraction assembly 16 so that needle 72 is towards injection end 18 and piston 56 is towards activation end 20. Once cartridge is installed in retraction assembly 16, the retraction assembly and injection assembly 12 can be operatively secured to one another. In the assembled state, injection assembly 12 and retraction assembly 16 preferably maintain cartridge 14 hermetically sealed therebetween.

As seen in FIG. 10, retraction assembly 16 includes a retraction spring 70, an end cap 76, a lower seal 78, a spring retainer 85, and tubular section 86. Before activation of syringe 10, retraction spring 70 is partially biased between spring retainer 85 and end cap 76. In the partially biased condition, retraction spring 70 urges spring retainer 85 in a direction opposite injection direction 48 to maintain the spring retainer abutted against surface 80. In this manner, spring retainer 85 maintains retraction spring 70 in a desired position in end cap 76 and prevents the retraction spring from falling out of retraction assembly 16 prior to assembly with injection assembly 12.

In addition, spring retainer 85 can include a needle guide channel 87. Channel 87 ensures that needle 72 of medicine cartridge 14 is properly inserted in retraction assembly 16. Spring retainer 85 can also include a bumper 89 to absorb and dampen impact during activation.

Advantageously, syringe 10 according to the present disclosure can be provided in an unassembled state in a terminally sterilized kit (not shown) for assembly and use. Here, the kit can include injection assembly 12, medicine cartridge 14 (FIG. 2 or FIG. 9), and retraction assembly 16 (FIG. 8 or FIG. 10). Thus, the kit allows a user or healthcare provider to prepare syringe 10 for use by simply placing medicine cartridge 14 in retraction assembly 16 and securing injection assembly 12 to the retraction assembly. In some embodiments, the kit can include one or more injection site cleaning swabs, such as pre-packaged alcohol swabs or other injection accessories such as an adhesive bandage.

Referring now to FIGS. 11 and 12, another exemplary embodiment of injection assembly 12 is shown. Again, syringe 10 is provided with injection assembly 12 separate from retraction assembly 16 for assembly by the user or healthcare provider. Advantageously, injection assembly 12 can include a safety element 110 for preventing injection spring 22 from ejecting plunger 24 from the injection assembly prior to assembly.

Safety element 110 provides a portion of plunger 24 with an outer dimension that is smaller than the inside diameter of injection spring 22, yet is larger than the inner dimension of de-coupler 28. Accordingly, safety element 110 prevents plunger 24 from escaping injection assembly 12 if the assembly is activated before final assembly with retraction assembly 16, while allowing proper movement of plunger 24 through injection spring 22.

In the embodiment illustrated in FIGS. 11 and 12, safety element 110 is illustrated as a ring, which is operatively connected about the circumference of plunger 24. Of course, it is contemplated by the present disclosure for safety element 110 to have other, non-ring shapes, that extend from only a portion of the circumference of plunger 24 in a location interposed between the coupling 30 and tines 40. In addition, it is contemplated for safety element 110 to be, as an alternative preferred embodiment, an integrally formed feature of plunger 24.

Figure 13:
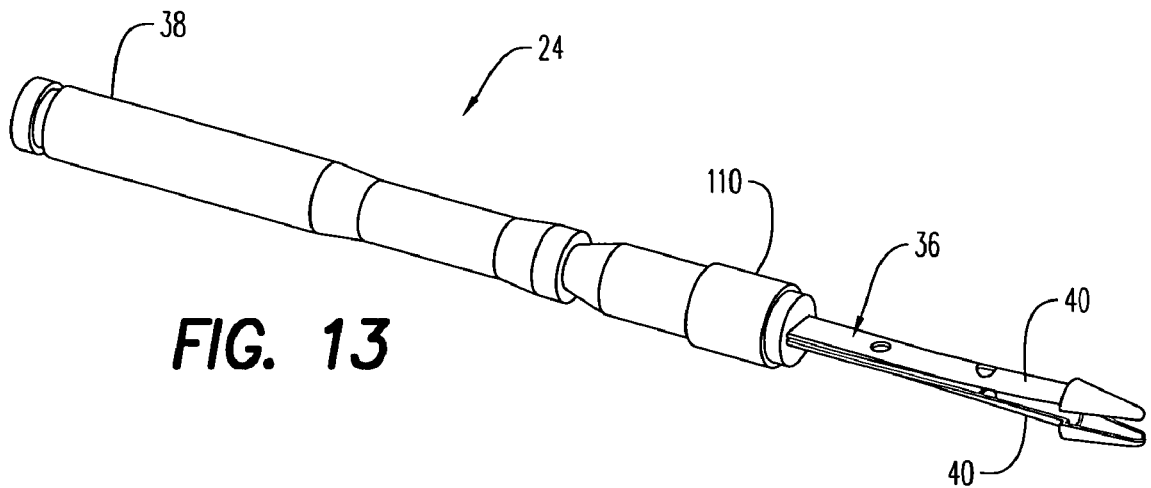
FIG. 13 is a perspective view of an alternate exemplary embodiment of a composite plunger according to the present disclosure.
Figure 14:
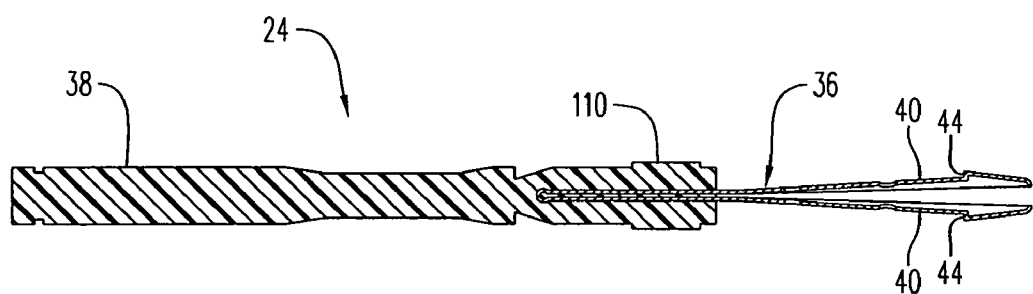
FIG. 14 is a sectional view of the composite plunger of FIG. 13.
Figure 15:
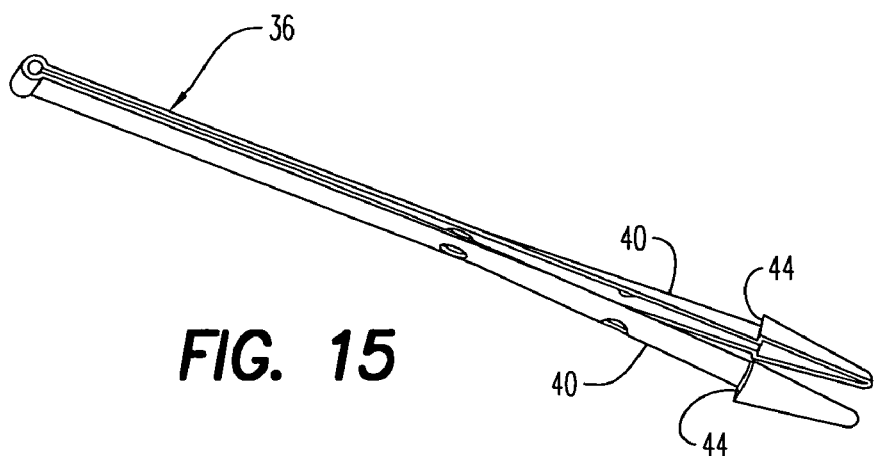
FIG. 15 is a perspective view of a stamped portion of the composite plunger of FIG. 13.

Referring now to FIGS. 13 through 15, an exemplary embodiment of a plunger according to the present disclosure is shown. As discussed above, plunger 24 includes locking end 36 and driving end 38. Locking end 36 includes fork tines 40 that are resiliently biased outward so that locking surface 44 engages capture 42 (FIG. 4) of power pack assembly 12. In this position, plunger 24 maintains injection spring 22 in a compressed or stressed condition. As such, locking end 36 includes sufficient resiliency to ensure that fork tines 40 are maintained in the outwardly biased position despite the forces of injection spring 22. In addition, locking end 36 includes sufficient structural rigidity to ensure locking surface 44 remain engaged with capture 42 despite the force of injection spring 22.

It has been determined by the present disclosure that a composite plunger as illustrated in FIGS. 13 through 15 provides the resiliency and structural rigidity properties as well as decreases the cost and manufacturing cycle time as compared to all metal plungers. The illustrated composite plunger 24 includes a metal locking end 36 and a plastic driving end 38.

During manufacture, metal locking end 36 can be defined by a common stamping operation from a flat supply of material. Next, metal locking end 36 can be bent to define tines 40. Once metal locking end 36 is completed, the metal locking end can be insert molded in plastic driving end 38 to define the composite plunger 24. In a preferred embodiment, molded plastic driving end 38 can include safety element 110 integrally molded therewith.

Figure 16:
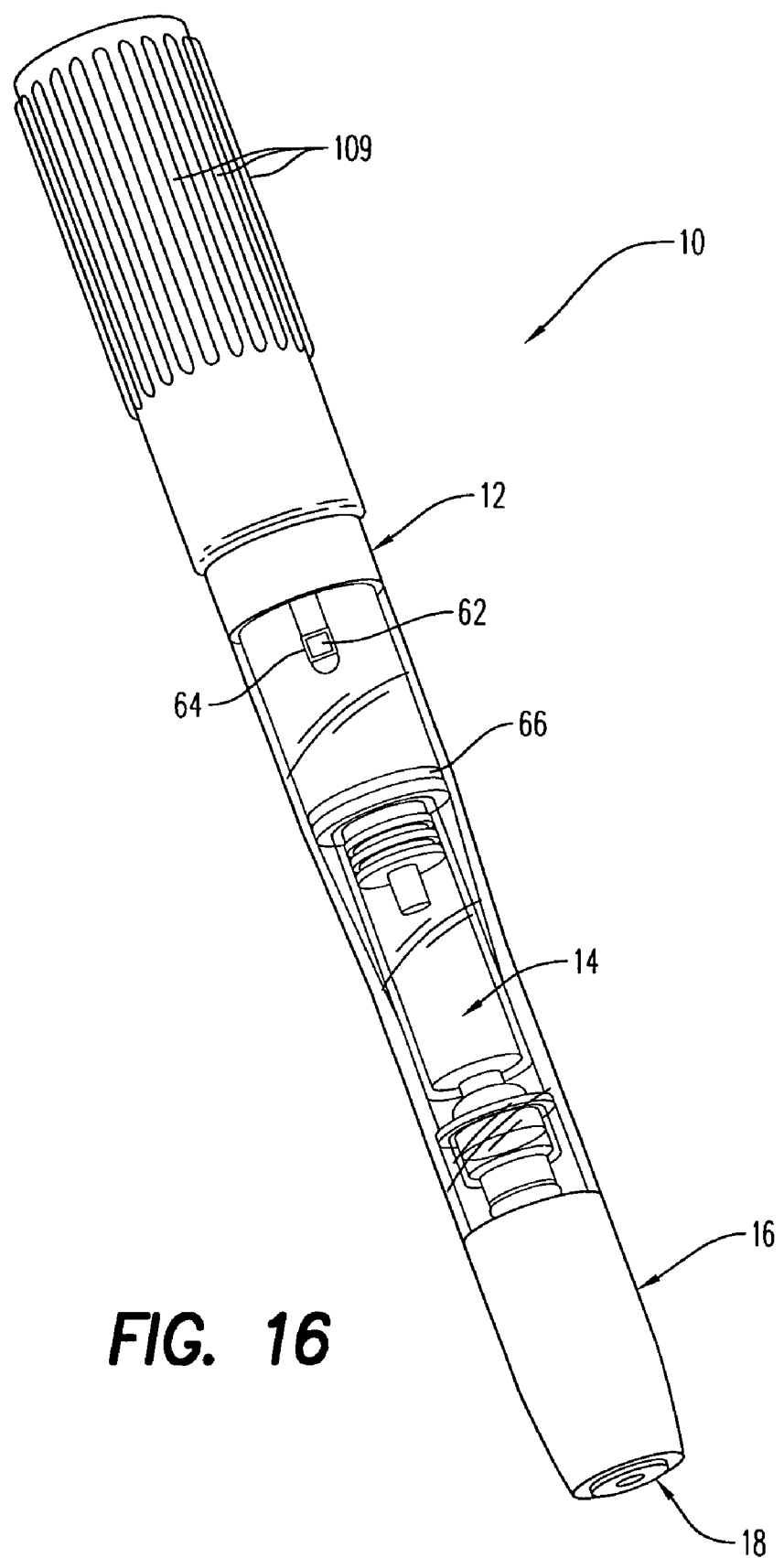
FIG. 16 is a perspective view of an alternate exemplary embodiment of a syringe according to the present disclosure.
Figure 17:
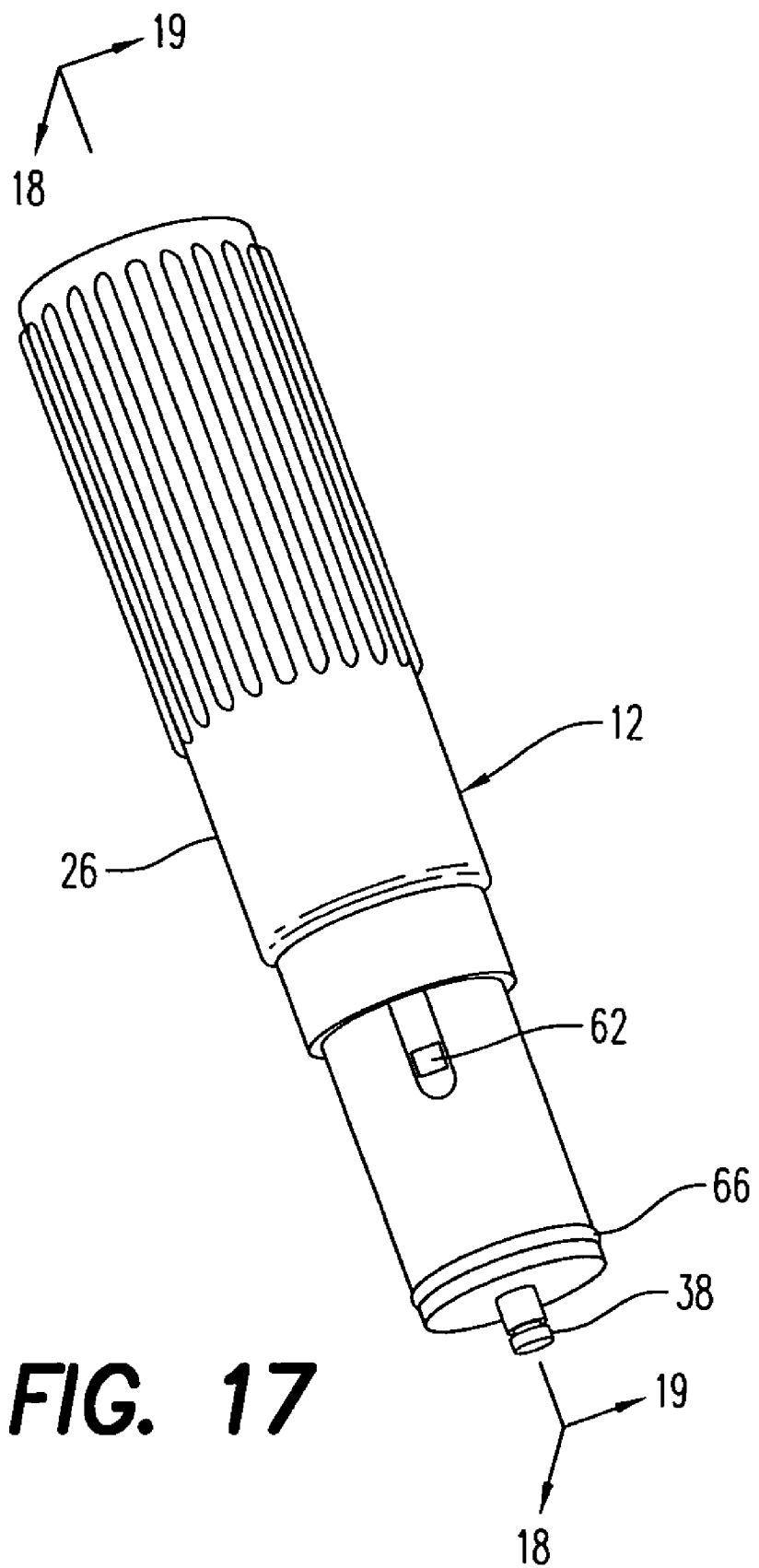
FIG. 17 is a perspective view of an injection assembly for use with the syringe of FIG. 16.
Figure 18:
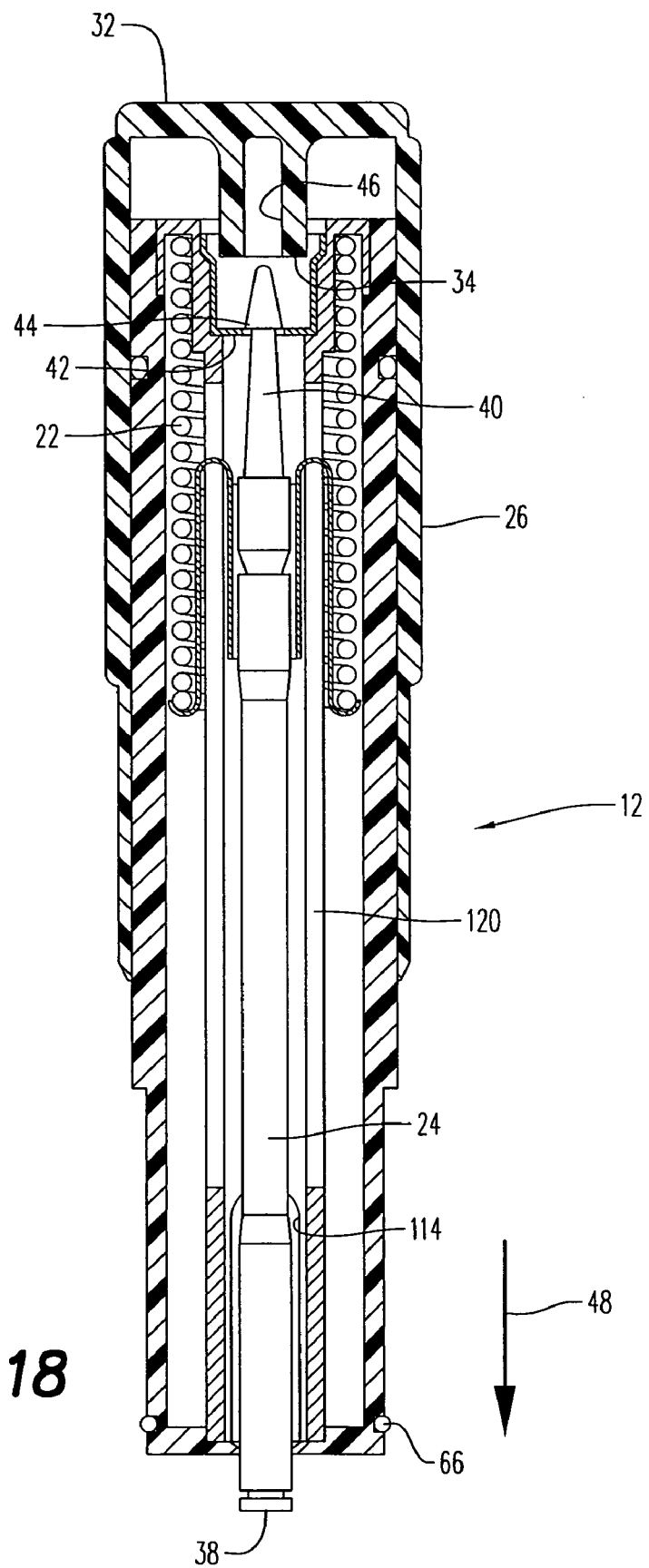
FIG. 18 is a first cross sectional view of the injection assembly of FIG. 17 taken along lines 18-18.

Referring now to FIG. 16, an alternate exemplary embodiment of a syringe 10 is shown in an assembled state. Again, syringe 10 includes an injection assembly 12, a medicine cartridge 14, and a retraction assembly 16 that can be assembled by the user or healthcare provider (e.g., pharmacist, doctor, nurse). Syringe 10 is particularly suited for intramuscular injections.

For purposes of brevity, medicine cartridge 14 and retraction assembly 16 are substantially as described with respect to FIGS. 1, 2, and 5 through 8. Additionally, the assembly of syringe 10 is substantially as is discussed above with reference to FIGS. 2.

However, the operation of the injection assembly 12 of FIG. 16 is described with reference to FIGS. 17 through 20.

Injection assembly 12 includes an injection spring 22, a plunger 24, an activation button 26, and a coupling 30. Injection spring 22 disposed about plunger 24 and is drivingly engaged to the plunger by coupling 30.

Activation button 26 has an upper end 32 and a lower end 34. Injection assembly 12 of syringe 10 is activated by grasping activation button 26 and depressing injection end 18 against the injection site. Depressing injection end 18 against the injection site while grasping activation button 26 causes the activation button to be depressed and, thus, to activate syringe 10.

In some embodiments, activation button 26 includes an outer shroud 108 to assist the user in gripping the activation button. In a preferred embodiment, shroud 108 can includes a number of longitudinal ribs 109 to assist the user in gripping activation button 26. In this manner, injection assembly 12 is particularly suited for use in situations where the user may lack typical manual dexterity, such as can be the case where the user is wearing protective gloves. In other embodiments, shroud 108 and/or longitudinal ribs 109 can be formed of elastomeric material to further assist the user in gripping injection assembly 12.

In other embodiments, outer shroud 108 and injection assembly 12 can include one or more cooperating guides (not shown) that permit depression of activation button 26 only after the activation device has been rotated to a predetermined position. In sum, outer shroud 108 and injection assembly 12 can work together to require movement in two directions, rotation and depression performed in sequence, in order to activate injection spring 22. Here, longitudinal ribs 109 can also assist the user in rotation.

Upper end 32 protrudes outwardly from injection assembly 12. Lower end 34 extends inwardly and configured to selectively disengage plunger 24 from capture 42 to allow injection spring 22 to drive plunger 24. In the illustrated embodiment, plunger 24 includes a locking end 36 and a driving end 38. Locking end 36 includes two or more tines 40 that are resiliently biased outward so that the tines are remote from one another. Driving end 38 is configured to act on medicine cartridge 14 as will be described in detail below.

Injection assembly 12 includes a capture 42 that engages a locking surface 44 of tines 40 when biased from one another. Activation button 26 includes a releasing surface 46 defined at lower end 34. Force applied to upper end 32 of activation button 26 in direction 48 while injection end 18 is held against the injection site causes releasing surface 46 to compress fork tines 40 toward one another such that locking surfaces 44 are disengaged from capture 42.

Prior to actuation, injection spring 22 is maintained in a normally biased or stressed condition between coupling 30 and capture 42. Upon release of tines 40 from capture 42, the stored energy in spring 22 propels plunger 24 in an injection direction 48.

Figure 19:
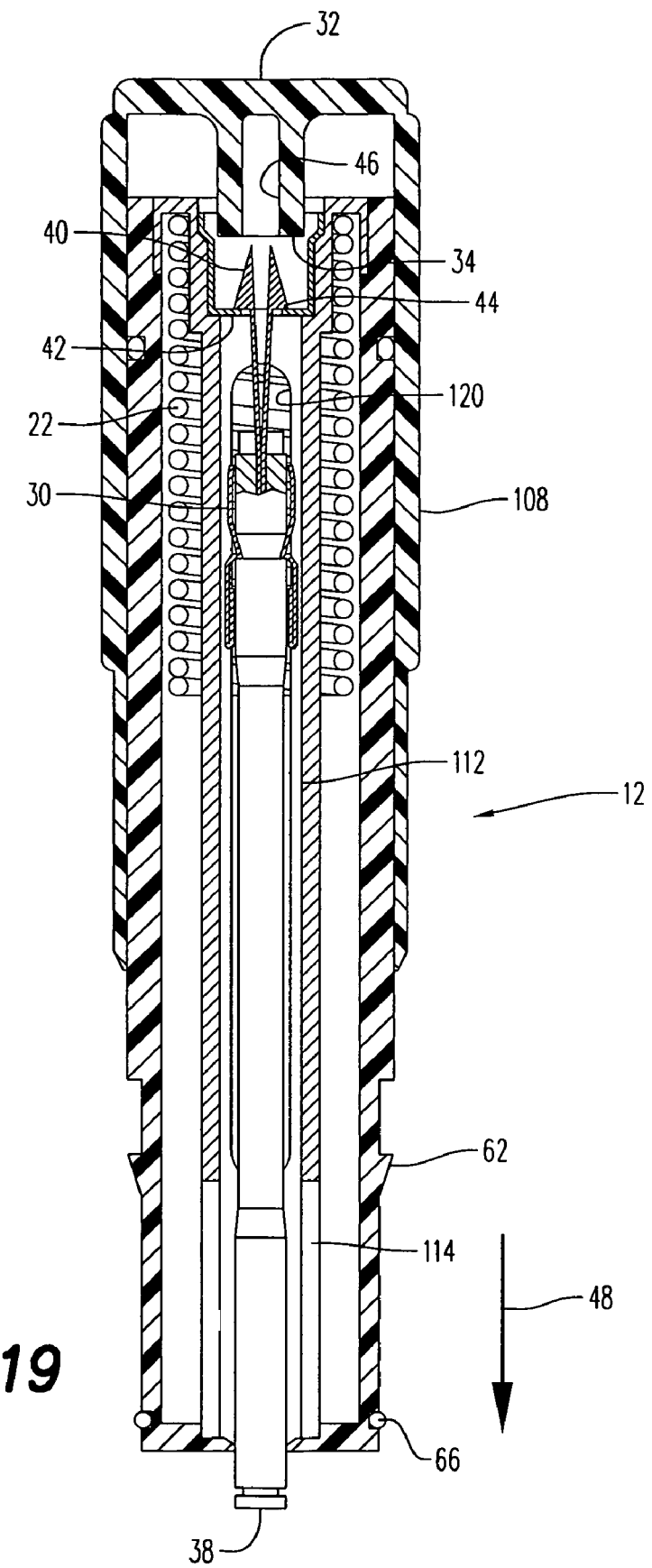
FIG. 19 is a second cross sectional view of the injection assembly of FIG. 17 taken along lines 19-19, where the injection assembly is shown before activation.
Figure 20:
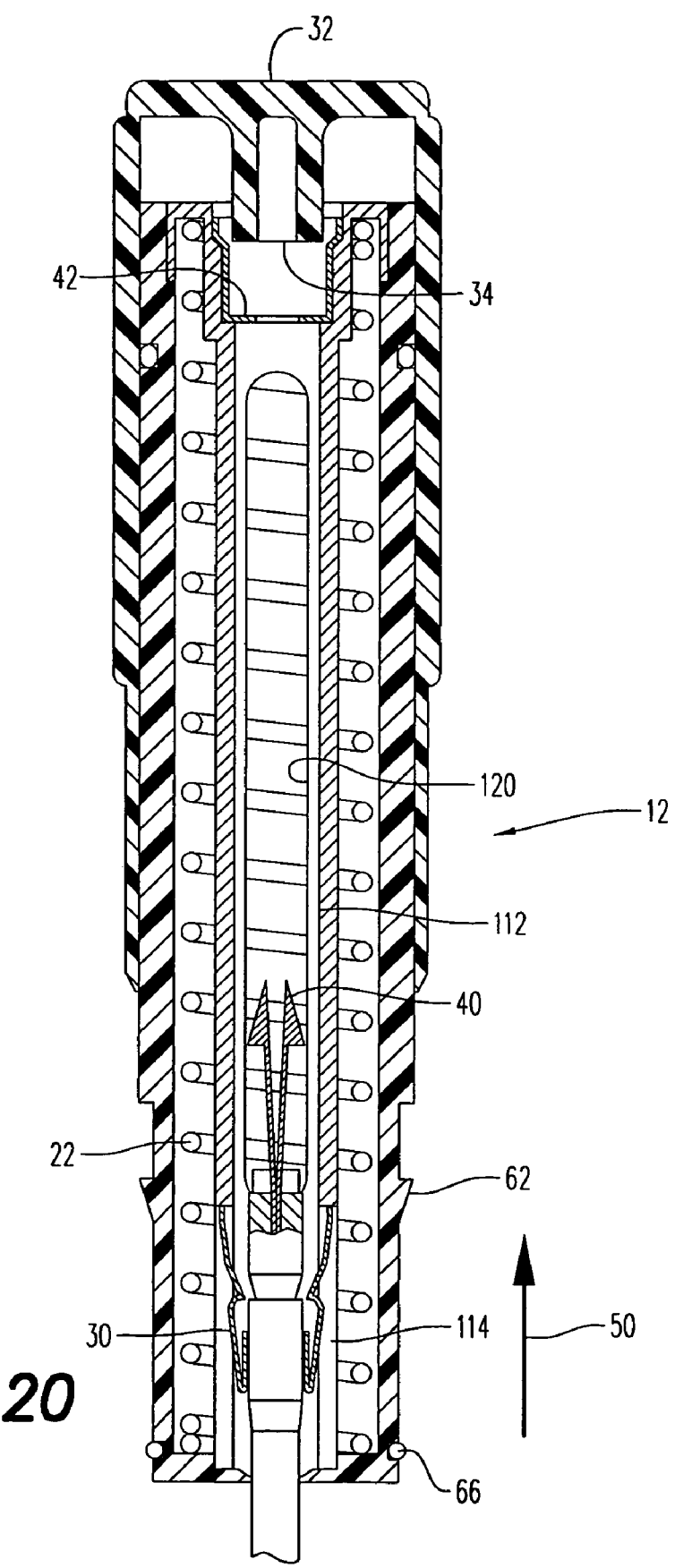
FIG. 20 is a view of the injection assembly of FIG. 19 shown after activation, and immediately prior to retraction.

Coupling 30 is an outwardly biased spring member and is described with particular reference to FIGS. 19 and 20. During assembly, coupling 30 is compressed inward towards plunger 24 until an internally disposed male feature of the coupling engages a corresponding female feature of the plunger. During the travel of plunger 24, coupling 30 maintains driving engagement between injection spring 22 and plunger 24.

Specifically, injection assembly 12 includes a passage 120 having a first inner diameter 112 that maintains sufficient radial constraint to maintain coupling 30 in the compressed position and engaged with plunger 24 as seen in FIG. 19. Passage 120 has an escapement 114 at the end of the stroke of plunger 24. Injection spring 22 drives plunger 24 in injection direction 48 until coupling 30 reaches escapement 114. The resiliency of coupling 30 causes the coupling to expand into escapements 14 and disengage from plunger 24 as seen in FIG. 20. The disengagement of coupling 30 from plunger 24 frees the plunger from the force of injection spring 22 and, thus, allows the plunger to be moved in a retraction direction 50 by retraction assembly 16.

Injection and retraction assemblies 12, 16 are secured to one another in a snap fit manner. For example, injection assembly 12 can include one or more outwardly depending tabs 62 that are received in a corresponding number of openings 64 defined in retraction assembly 16. In the assembled state, injection assembly 12 and retraction assembly 16 maintain cartridge 14 hermetically sealed therebetween by way of, for example, a sealing member 66.

It should also be noted that the terms "first", "second", "third", "upper", "lower", and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

What is claimed is:

1. An injection and retraction syringe, comprising:
a medicine cartridge;
an injection assembly; and
a retraction assembly being selectively securable to said injection assembly to house said medicine cartridge therein, said retraction assembly comprising:
an end cap,
a hypodermic needle having a needle hub,
a retraction spring disposed between said needle hub and said end cap and maintained in a partially compressed condition therebetween, and
an upper seal urged against a facially sealing surface perpendicular to a radial sealing surface of an inner diameter of said retraction assembly by said retraction spring in said partially compressed condition to form a first hermetic seal.

2. The syringe of claim 1, further comprising a lower seal defining a sealed volume between said upper and lower seals, said hypodermic needle being disposed in said sealed volume.

3. The syringe of claim 2, wherein sealed volume is sterile.

4. The syringe of claim 1, wherein said upper seal forms a second hermetic seal with a radial sealing surface of said retraction assembly.

5. An injection and retraction syringe, comprising;
a medicine cartridge;
an injection assembly;
a retraction assembly being selectively securable to said injection assembly to house said medicine cartridge therein, said retraction assembly comprising:
an end cap,
a hypodermic needle having a needle hub,
a retraction spring disposed between said needle hub and said end cap and maintained in a partially compressed condition therebetween, and
an upper seal urged against a facially sealing surface of said retraction assembly by said retraction spring in said partially compressed condition to form a first hermetic seal; and
an o-ring member forming a second hermetic seal between said retraction assembly and said injection assembly when said retraction assembly is secured to said injection assembly.

6. An injection and retraction syringe comprising:
a medicine cartridge;
an injection assembly;
a retraction assembly being selectively securable to said injection assembly to house said medicine cartridge therein, said retraction assembly comprising:
an end cap,
a hypodermic needle having a needle hub,
a retraction spring disposed between said needle hub and said end cap and maintained in a partially compressed condition therebetween, and
an upper seal urged against a facially sealing surface of said retraction assembly by said retraction spring in said partially compressed condition to form a first hermetic seal; and
wherein said injection assembly comprises one or more outwardly depending tabs for receipt in a corresponding number of openings defined in said retraction assembly when said retraction assembly is secured to said injection assembly.

* * * * *